(12) United States Patent
Staniforth

(10) Patent No.: US 7,718,163 B2
(45) Date of Patent: *May 18, 2010

(54) CARRIER PARTICLES FOR USE IN DRY POWDER INHALERS

(75) Inventor: John Nicholas Staniforth, Bath (GB)

(73) Assignee: Vectura Limited (01696917), Wiltshire (GB)

(*) Notice: Subject to any disclaimer, the term of this patent is extended or adjusted under 35 U.S.C. 154(b) by 76 days.

This patent is subject to a terminal disclaimer.

(21) Appl. No.: 11/202,741

(22) Filed: Aug. 11, 2005

(65) Prior Publication Data

US 2006/0029552 A1 Feb. 9, 2006

Related U.S. Application Data

(63) Continuation of application No. 10/306,865, filed on Nov. 27, 2002, now Pat. No. 7,011,818, which is a continuation of application No. 09/680,863, filed on Oct. 6, 2000, now Pat. No. 6,521,260, which is a continuation of application No. 08/875,391, filed as application No. PCT/GB96/00215 on Jan. 31, 1996, now Pat. No. 6,153,224.

(30) Foreign Application Priority Data

| Jan. 31, 1995 | (GB) | ............................. 9501841.2 |
| Oct. 26, 1995 | (GB) | ............................. 9521937.4 |

(51) Int. Cl.
| A61K 9/14 | (2006.01) |
| A61K 9/16 | (2006.01) |
| A61K 31/195 | (2006.01) |
| A61K 38/00 | (2006.01) |

(52) U.S. Cl. .................... 424/46; 424/489; 424/490; 424/493; 514/951; 514/2

(58) Field of Classification Search .................... 424/46, 424/489, 490, 493; 514/951, 2
See application file for complete search history.

(56) References Cited

U.S. PATENT DOCUMENTS

| 2,533,065 | A | 12/1950 | Taplin et al. |
| 3,957,965 | A | 5/1976 | Hartley et al. |
| 5,376,386 | A | 12/1994 | Ganderton et al. |
| 5,478,578 | A | 12/1995 | Arnold et al. |
| 5,506,203 | A | 4/1996 | Backstrom et al. |
| 5,642,728 | A | 7/1997 | Andersson et al. |
| 5,972,388 | A | 10/1999 | Sakon et al. |
| 6,153,224 | A | 11/2000 | Staniforth |
| 6,521,260 | B1 | 2/2003 | Staniforth |
| 6,884,794 | B2 * | 4/2005 | Staniforth et al. ........... 514/170 |
| 7,223,748 | B2 * | 5/2007 | Staniforth et al. ........... 514/174 |
| 2003/0133880 | A1 | 7/2003 | Musa et al. |
| 2003/0175214 | A1 * | 9/2003 | Staniforth et al. ............. 424/46 |
| 2003/0185764 | A1 * | 10/2003 | Staniforth et al. ............. 424/46 |

FOREIGN PATENT DOCUMENTS

| EP | 0 124 493 | 11/1984 |
| EP | 187 433 | 7/1986 |
| EP | 239 798 | 10/1987 |
| EP | 0606486 A1 * | 7/1994 |
| GB | 786499 | 11/1957 |
| GB | 905723 | 9/1962 |
| GB | 1 132 583 | 11/1968 |
| GB | 1 230 087 | 4/1971 |
| GB | 1 242 211 | 8/1971 |
| GB | 1 242 212 | 8/1971 |
| GB | 1310527 | 3/1973 |
| GB | 1 381 872 | 1/1975 |
| GB | 2240337 | 7/1991 |
| GB | 2 269 992 | 3/1994 |
| SE | 9203743-1 | 10/1993 |
| WO | WO 87/05213 | 9/1987 |
| WO | WO 91/11173 | 8/1991 |
| WO | WO 91/14422 | 10/1991 |
| WO | WO 92/08447 | 5/1992 |
| WO | WO 93/11746 | 12/1992 |
| WO | WO 93/11746 | 6/1993 |
| WO | WO 94/04133 | 3/1994 |
| WO | WO 94/13271 | 6/1994 |
| WO | WO 95/00127 | 1/1995 |
| WO | WO 95/00128 | 1/1995 |
| WO | WO 95/11666 | 5/1995 |
| ZA | 9 400 155 | 1/1994 |

OTHER PUBLICATIONS

Lieberman et al, Pharmaceutical Dosage Forms (Marcel Dekker, INC), vol. 2, 1981, pp. 77-85.*
Ganderton. "The Generation of Respirable clouds form coarse powder aggregates." *Journal of Biopharmaceutical Sciences*. vol. 3(1/2). 1992. pp. 101-105.
Kassem. "Generation of Deeply Inspirable clouds from dry power mixtures." *PhD Thesis. Department of Pharmacy. Kings College: University of London*. 1990. pp. 1-275.
Ahmed, Hashim Abdalla. "Particle Interactions in Multicomponent Systems" (Ph. D. Thesis, University of Bath, 1989), pp. I-376.
Glaxo Opposition Against European Patent 1232745 In the Name of Vectura Limited, Aug. 24, 2009.
Norton Opposition Against European patent No. 1 232 745, Norton Healthcare Ltd. Aug. 10, 2009.
European Search Report —corresponding application no. Ep 06 08 4066. Mailed Mar. 26, 2009.

* cited by examiner

*Primary Examiner*—Mina Haghighatian
(74) *Attorney, Agent, or Firm*—Merchant & Gould P.C.

(57) ABSTRACT

A powder for use in a dry powder inhaler includes active particles and carrier particles for carrying the active particles. The powder further includes additive material (4) on the surfaces of the carrier particles to promote the release of the active particles from the carrier particles on actuation of the inhaler. The powder is such that the active particles are not liable to be release from the carrier particles before actuation of the inhaler. The inclusion of additive material (4) in the powder has been found to give an increased respirable fraction of the active material.

45 Claims, 2 Drawing Sheets

CARRIER PARTICLES FOR USE IN DRY POWDER INHALERS

Figure 1:
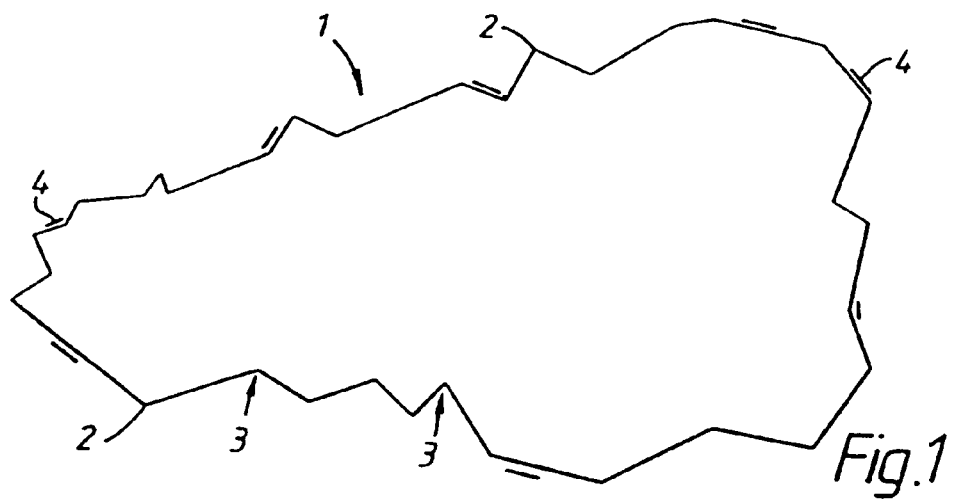
Figure 4A:
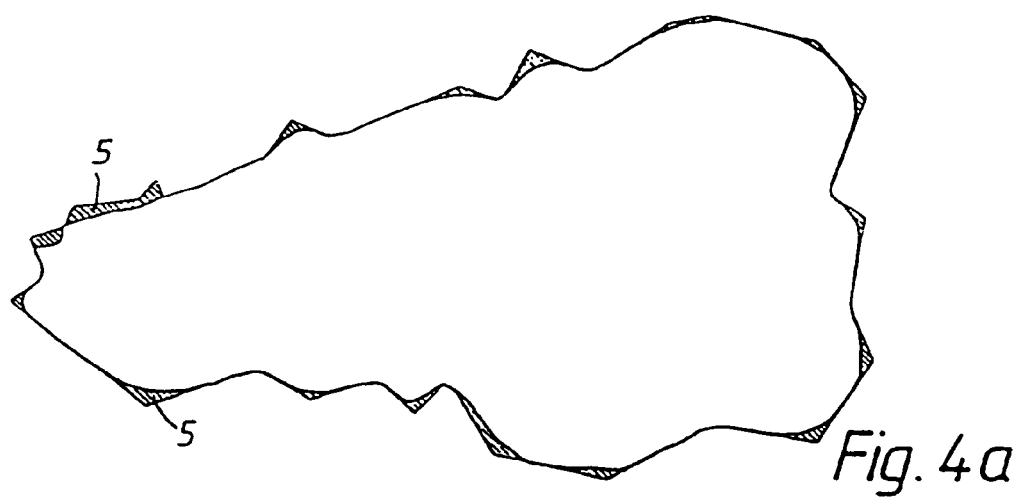
Figure 4B:
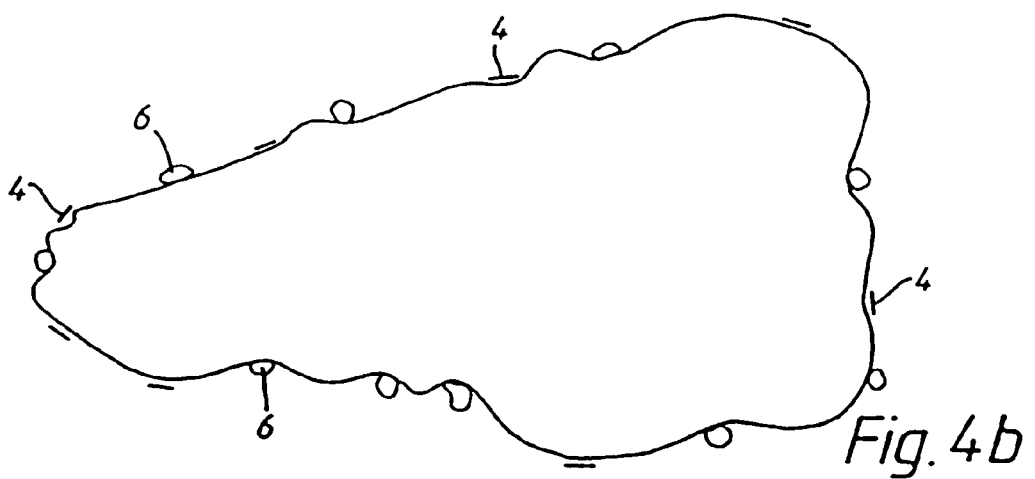

This application is a Continuation of application Ser. No. 10/306,865, filed Nov. 27, 2002, which is a Continuation of application Ser. No. 09/680,863 filed Oct. 6, 2000, which is a Continuation of application Ser. No. 08/875,391 filed Sep. 25, 1997, which is the National Stage of Application PCT/GB96/00215, filed Jan. 31, 1996, and which application(s) are incorporated herein by reference.

This invention relates to carrier particles for use in dry powder inhalers. More particularly the invention relates to a method of producing such particles, to a dry powder incorporating the particles and to the particles themselves.

Inhalers are well known devices for administering pharmaceutical products to the respiratory tract by inhalation. Inhalers are widely used particularly in the treatment of diseases of the respiratory tract.

There are a number of types of inhaler currently available. The most widely used type is a pressurised metered dose inhaler (MDI) which uses a propellant to expel droplets containing the pharmaceutical product to the respiratory tract. Those devices are disadvantageous on environmental grounds as they often use CFC propellants, and on clinical grounds related to the inhalation characteristics of the devices.

An alternative device to the MDI is the dry powder inhaler. The delivery of dry powder particles of pharmaceutical products to the respiratory tract presents certain problems. The inhaler should deliver the maximum possible proportion of the active particles expelled to the lungs, including a significant proportion to the lower lung, preferably at the low inhalation capabilities to which some patients, especially asthmatics, are limited. It has been found, however, that, when currently available dry powder inhaler devices are used, in many cases only about 10% of the active particles that leave the device on inhalation are deposited in the lower lung. More efficient dry powder inhalers would give clinical benefits.

The type of dry powder inhaler used is of significant importance to the efficiency of delivery over a range of airflow conditions of the active particles to the respiratory tract. Also, the physical properties of the active particles used affect both the efficiency and reproducibility of delivery of the active particles and the site of deposition in the respiratory tract.

On exit from the inhaler device, the active particles should form a physically and chemically stable aerocolloid which remains in suspension until it reaches a conducting bronchiole or smaller branching of the pulmonary tree or other absorption site preferably in the lower lung. Once at the absorption site, the active particle should be capable of efficient collection by the pulmonary mucosa with no active particles being exhaled from the absorption site.

The size of the active particles is important. For effective delivery of active particles deep into the lungs, the active particles should be small, with an equivalent aerodynamic diameter substantially in the range of 0.1 to 5 μm, approximately spherical and monodispersed in the respiratory tract. Small particles are, however, thermodynamically unstable due to their high surface area to volume ratio, which provides significant excess surface free energy and encourages particles to agglomerate. In the inhaler, agglomeration of small particles and adherence of particles to the walls of the inhaler are problems that result in the active particles leaving the inhaler as large agglomerates or being unable to leave the inhaler and remaining adhered to the interior of the inhaler.

The uncertainty as to the extent of agglomeration of the particles between each actuation of the inhaler and also between different inhalers and different batches of particles, leads to poor dose reproducibility. It has been found that powders are reproducibly fluidisable, and therefore reliably removable from an inhaler device, when the particles have a diameter greater than 90 μm.

To give the most effective dry powder aerosol, therefore, the particles should be large while in the inhaler, but small when in the respiratory tract.

In an attempt to achieve that situation, one type of dry powder for use in dry powder inhalers may include carrier particles to which the fine active particles adhere whilst in the inhaler device, but which are dispersed from the surfaces of the carrier particles on inhalation into the respiratory tract to give a fine suspension. The carrier particles are often large particles greater than 90 μm in diameter to give good flow properties as indicated above. Small particles with a diameter of less than 10 μm may be deposited on the wall of the delivery device and have poor flow and entrainment properties leading to poor dose uniformity.

The increased efficiency of redispersion of the fine active particles from the agglomerates or from the surfaces of carrier particles during inhalation is regarded as a critical step in improving the efficiency of the dry powder inhalers.

It is known that the surface properties of a carrier particle are important. The shape and texture of the carrier particle should be such as to give sufficient adhesion force to hold the active particles to the surface of the carrier particle during fabrication of the dry powder and in the delivery device before use, but that force of adhesion should be low enough to allow the dispersion of the active particles in the respiratory tract.

In order to reduce the force of adhesion between carrier particles and active particles, it has been proposed to add a ternary component. In particular, using carrier particles of lactose and active particles of salbutamol, it has been proposed to add particles of magnesium stearate or Aerosil 200 (trade name of Degussa for colloidal silicon dioxide) in an amount of 1.5% by weight based on the weight of the carrier particles to a lactose-salbutamol mix.

The conclusion of that proposal, however, was that, although the adhesion between the carrier particles and the active particles was reduced by the presence of the additive particles, the, addition of the additive particles was undesirable.

It is an object of the invention to provide a method for producing carrier particles and a powder for use in dry powder inhalers, and to provide carrier particles and a powder that mitigates the problems referred to above.

We have found that, contrary to the teaching of the prior art referred to above, the presence of additive particles which are attached to the surfaces of the carrier particles to promote the release of the active particles from the carrier particles is advantageous provided that the additive particles are not added in such a quantity that the active particles segregate from the surfaces of the carrier particles during fabrication of the dry powder and in the delivery device before use. Furthermore, we have found that the required amount of the additive particles is surprisingly small and that, if a greater amount is added, there will be no additional benefit in terms of inhalation performance but it will adversely affect the ability to process the mix. The required amount of additive particles varies according to the composition of the particles—in the case where the additive particles are of magnesium stearate (that being a material that may be used but is not preferred), we have found that an amount of 1.5 per cent by weight based on the total weight of the powder is too great and causes premature segregation of the active particles from the carrier particles. We believe that the same considerations apply in the case of Aerosil 200.

The present invention provides a powder for use in a dry powder inhaler, the powder including active particles and carrier particles for carrying the active particles, the powder further including additive material on the surfaces of the carrier particles to promote the release of the active particles from the carrier particles on actuation of the inhaler, the powder being such that the active particles are not liable to be released from the carrier particles before actuation of the inhaler.

"Actuation of the inhaler" refers to the process during which a dose of the powder is removed from its rest position in the inhaler, usually by a patient inhaling. That step takes place after the powder has been loaded into the inhaler ready for use.

In this specification we give many examples of powders for which the amount of the additive material is so small that the active particles are not liable to be released from the carrier particles before actuation of the inhaler but are released during use of the inhaler. If it is desired to test whether or not the active particles of a powder are liable to be released from the carrier particles before actuation of the inhaler a test can be carried out. A suitable test is described at the end of this specification; a powder whose post-vibration homogeneity measured as a percentage coefficient of variation, after being subjected to the described test, is less than about 5% can be regarded as acceptable. In an example of the invention described below the coefficient is about 2% which is excellent, whereas in an example also described below and employing 1.5% by weight of magnesium stearate the coefficient is about 15% which is unacceptable.

The surface of a carrier particle is not usually smooth but has asperities and clefts in its surface. The site of an asperity or of a cleft is believed to be an area of high surface energy. The active particles are preferentially attracted to and adhere most strongly to those high energy sites causing uneven and reduced deposition of the active particles on the carrier surface. If an active particle adheres to a high energy site, it is subjected to a greater adhesion force than a particle at a lower energy site on the carrier particle and will therefore be less likely to be able to leave the surface of the carrier particle on actuation of the inhaler and be dispersed in the respiratory tract. It would therefore be highly advantageous to decrease the number of those high energy sites available to the active particles.

Additive material is attracted to and adheres to the high energy sites on the surfaces of the carrier particles. On introduction of the active particles, many of the high energy sites are now occupied, and the active particles therefore occupy the lower energy sites on the surfaces of the carrier particles. That results in the easier and more efficient release of the active particles in the airstream created on inhalation, thereby giving increased deposition of the active particles in the lungs.

However, as indicated above, it has been found that the addition of more than a small amount of additive material is disadvantageous because of the adverse effect on the ability to process the mix during commercial manufacture.

It is also advantageous for as little as possible of the additive material to reach the lungs on inhalation of the powder. Although the additive material will most advantageously be one that is safe to inhale into the lungs, it is still preferred that only a very small proportion, if any, of the additive material reaches the lung, in particular the lower lung. The considerations that apply when selecting the additive material and other features of the powder are therefore different from the considerations when a third component is added to carrier and active material for certain other reasons, for example to improve absorption of the active material in the lung, in which case it would of course be advantageous for as much as possible of the additive material in the powder to reach the lung.

In the present case, as indicated above, there will be an optimum amount of additive material, which amount will depend on the chemical composition and other properties of the additive material. However, it is thought that for most additives the amount of additive material in the powder should be not more than 10%, more advantageously not more than 5%, preferably not more than 4% and for most materials will be not more than 2% or less by weight based on the weight of the powder. In certain Examples described below the amount is about 1%.

Advantageously the additive material is an anti-adherent material and will tend to decrease the cohesion between the active particles and the carrier particles.

Advantageously the additive material is an anti-friction agent (glidant) and will give better flow of powder in the dry powder inhaler which will lead to better dose reproducibility from the inhaler.

Where reference is made to an anti-adherent material, or to an anti-friction agent, the reference is to include those materials which will tend to decrease the cohesion between the active particles and the carrier particles, or which will tend to improve the flow of powder in the inhaler, even though they may not usually be referred to as an anti-adherent material or an anti-friction agent. For example, leucine is an anti-adherent material as herein defined and is generally thought of as an anti-adherent material but lecithin is also an anti-adherent material as herein defined, even though it is not generally thought of as being anti-adherent, because it will tend to decrease the cohesion between the active particles and the carrier particles.

The carrier particles may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of lactose.

Advantageously, substantially all (by weight) of the carrier particles have a diameter which lies between 20 μm and 1000 μm, more preferably 50 μm and 1000 μm. Preferably, the diameter of substantially all (by weight) of the carrier particles is less than 355 μm and lies between 20 μm and 250 μm. Preferably at least 90% by weight of the carrier particles have a diameter between from 60 μm to 180 μm. The relatively large diameter of the carrier particles improves the opportunity for other, smaller particles to become attached to the surfaces of the carrier particles and to provide good flow and entrainment characteristics and improved release of the active particles in the airways to increase deposition of the active particles in the lower lung.

It will be understood that, throughout, the diameter of the particles referred to is the aerodynamic diameter of the particles.

Advantageously, the additive material consists of physiologically acceptable material. As already indicated, it is preferable for only small amounts of additive material to reach the lower lung, and it is also highly preferable for the additive material to be a material which may be safely inhaled into the lower lung where it may be absorbed into the blood stream. That is especially important where the additive material is in the form of particles.

The additive material may include a combination of one or more materials.

It will be appreciated that the chemical composition of the additive material is of particular importance.

Preferably the additive material is a naturally occurring animal or plant substance.

Advantageously the additive material includes one or more compounds selected from amino acids and derivatives thereof, and peptides and polypeptides having molecular weight from 0.25 to 1000 KDa, and derivatives thereof. Amino acids, peptides or polypeptides and their derivatives are both physiologically acceptable and give acceptable release of the active particles on inhalation.

It is particularly advantageous for the additive material to comprise an amino acid. Amino acids have been found to give, when present in low amounts in the powders as additive material, high respirable fraction of the active materials with little segregation of the powder and also with very little of the amino acid being transported into the lower lung. In respect of leucine, a preferred amino acid, it is found that, for example, for an average dose of powder only about 10 μg of leucine would reach the lower lung. The additive material may comprise one or more of any of the following amino acids: leucine, isoleucine, lysine, valine, methionine, phenylalanine. The additive may be a salt or a derivative of an amino acid, for example aspartame or acesulfame K. Preferably the additive particles consist substantially of leucine, advantageously L-leucine. As indicated above, leucine has been found to give particularly efficient release of the active particles on inhalation. Whilst the L-form of the amino acids is used in Examples described below, the D- and DL-forms may also be used.

The additive material may include one or more water soluble substances. This helps absorption of the substance by the body if the additive reaches the lower lung. The additive material may include dipolar ions, which may consist of zwitterions.

Alternatively, the additive material may comprise particles of a phospholipid or a derivative thereof. Lecithin has been found to be a good material for the additive material.

The additive material may include or consist of one or more surface active materials, in particular materials that are surface active in the solid state, which may be water soluble, for example lecithin, in particular soya lecithin, or substantially water insoluble, for example solid state fatty acids such as lauric acid, palmitic acid, stearic acid, erucic acid, behenic acid, or derivatives (such as esters and salts) thereof. Specific examples of such materials are: magnesium stearate; sodium stearyl fumarate; sodium stearyl lactylate; phosphatidylcholines, phosphatidylglycerols and other examples of natural and synthetic lung surfactants; Liposomal formulations; lauric acid and its salts, for example, sodium lauryl sulphate, magnesium lauryl sulphate; triglycerides such as Dynsan 118 and Cutina HR; and sugar esters in general.

Other possible additive materials include talc, titanium dioxide, aluminium dioxide, silicon dioxide and starch.

As indicated above, it is most important for the additive material to be added in a small amount. For example, magnesium stearate is highly surface active and should therefore be added in particularly small amounts; phosphatidylcholines and phosphatidylglycerols on the other hand are less active and can usefully be added in greater amounts; in respect of leucine, which is still less active, an addition of 2% by weight leucine based on the weight of the powder gives good results in respect of the respirable fraction of the active particles, low segregation and low amount of leucine reaching the lower lung; an addition of a greater amount does not improve the results and in particular does not significantly improve the respirable fraction and therefore whilst even with 6% leucine a reasonable result is obtained that is not preferred since it results in an increased quantity of additive material being taken into the body and will adversely affect the processing properties of the mix.

The additive material will often be added in particulate form but it may be added in liquid or solid form and for some materials, especially where it may not be easy to form particles of the material and/or where those particles should be especially small, it may be preferred to add the material in a liquid, for example as a suspension or a solution. Even then, however, the additive material of the finished powder may be in particulate form. An alternative possibility, however, that is within the scope of the invention is to use an additive material which remains liquid even in the final essentially particulate material which can still be described as a "dry powder".

In some cases improved clinical benefits will be obtained where the additive material is not in the form of particles of material. In particular, the additive material is less likely to leave the surface of the carrier particle and be transported into the lower lung.

Where the additive material of the finished powder is particulate, the nature of the particles may be significant. The additive particles may be non-spherical in shape. In Examples 1 to 3 below, the additive particles are plate-like particles. Alternatively the additive particles may be angular for example prisms, or dendritic in shape. Additive particles which are non-spherical may be easier to remove from the surfaces of the carrier particles than spherical, non-angular particles and plate-like particles may give improved surface interaction and glidant action between the carrier particles.

The surface area of the additive particles is also thought to be important. The surface area of the additive particles, as measured using gas absorption techniques, is preferably at least $5 \text{ m}^2\text{g}^{-1}$. In many cases it is found that additive material comprising small plate-like particles is preferred.

Advantageously, at least 95% by weight of the additive particles have a diameter less than 150 μm, more advantageously less than 100 μm, preferably less than 50 μm. Preferably, the mass median diameter of the additive particles is not more than about 10 μm. The additive particles preferably have a mass median diameter less than the mass median diameter of the carrier particles and will usually have a mass median diameter of approximately between a tenth and a hundredth that of the carrier particles. The diameter of the particles may be calculated by laser diffraction or by another method by which the aerodynamic diameter of the particles can be determined.

The ratio in which the carrier particles, additive material and active particles are mixed will, of course, depend on the type of inhaler device used, the type of active particles used and the required dose. As indicated above, the amount of additive material is of particular importance. Advantageously the amount is in the range of from 0.1 to 10% by weight of the additive material based on the weight of the carrier particles. For the examples given below, the powder preferably consists of not less than 0.1% by weight of additive material based on the weight of the carrier particles and the powder preferably consists of at least 0.1% by weight of active particles based on the weight of the powder. Furthermore, the carrier particles are preferably present in an amount of at least 90%, more preferably at least 95%, by weight based on the weight of the powder.

Conventional calculations of the extent of surface coverage of the carrier particles by the additive material shows that for the preferred carrier particles and preferred additive materials mixed in their preferred amounts, the amount of additive material is much more than that necessary to provide a monolayer coating of the carrier particle. For example, in the case of Example 1 described below, calculation shows that a small fraction of a percent of leucine by weight is sufficient to provide a monolayer coating, whereas 1% leucine by weight is employed. Furthermore, it is found that even with 1% leucine there is no "coating" of the carrier particles in the sense in which that word is normally used in the art, namely to refer to a continuous envelope around the carrier particle; rather inspection of the carrier particles under an electron microscope shows much of the surface of each lactose particle remaining exposed with leucine particles covering only limited portions of each lactose particle and forming a discontinuous covering on each lactose particle. It is believed that the presence of such a discontinuous covering, as opposed to a "coating" is an important and advantageous feature of the present invention.

Preferably the additive material, whilst providing only a discontinuous covering for the carrier particles, does saturate the surfaces of the carrier particles in the sense that even if more additive material were provided substantially the same covering of the carrier particles would be achieved. When the additive material in the finished powder is particulate, some of the additive particles, either individually or as agglomerates, may act as carriers of active particles and may be separate from or may separate from the surfaces of the carrier particles with active particles attached to their surfaces. The dimensions of the combined active particle and additive particle may still be within the optimum values for good deposition in the lower lung. It is believed that active particles which adhere to the additive particles on the carrier particles may in some cases be preferentially released from the surfaces of the carrier particles and thereafter be deposited in the lower lung without the additive particles.

Advantageously, the mass median diameter of the active particles is not more than 10 µm, preferably not more than 5 µm. The particles therefore give a good suspension on redispersion from the carrier particles and are delivered deep into the respiratory tract. Where the active particles are not spherical, the diameter of the particles may be calculated by laser diffraction or another method by which the aerodynamic diameter of the particles can be determined.

The active material referred to throughout the specification will be material of one or a mixture of pharmaceutical product(s). It will be understood that the term "active material" includes material which is biologically active, in the sense that it is able to increase or decrease the rate of a process in a biological environment. The pharmaceutical products include those products which are usually administered orally by inhalation for the treatment of disease such as respiratory disease eg. β-agonists, salbutamol and its salts, salmeterol and its salts. Other pharmaceutical products which could be administered using a dry powder inhaler include peptides and polypeptides, such as DNase, leucotrienes and insulin.

The active particles may include a $\beta_2$-agonist which may be terbutaline, a salt of terbutaline, for example terbutaline sulphate, or a combination thereof or may be salbutamol, a salt of salbutamol or a combination thereof. Salbutamol and its salts are widely used in the treatment of respiratory disease. The active particles may be particles of salbutamol sulphate. The active particles may be particles of ipatropium bromide.

The active particles may include a steroid, which may be beclomethasone dipropionate or may be Fluticasone. The active principle may include a cromone which may be sodium cromoglycate or nedocromil. The active principle may include a leukotriene receptor antagonist.

The active particles may include a carbohydrate, for example heparin.

According to the invention, there are provided particles for use in a powder as described above, the particles including carrier particles of a first composition and of a size suitable for use in a dry powder inhaler and additive material of a second composition, the additive material being attached to the surfaces of the carrier particles.

In a general aspect, the invention also provides a powder for use in a dry powder inhaler, the powder including active particles and carrier particles for carrying the active particles wherein the powder further includes additive material which is attached to the surfaces of the carrier particles to promote the release of the active particles from the carrier particles.

According to the invention, there is also provided a method of producing particles suitable for use as particles in dry powder inhalers, the method including the step of mixing carrier particles of a size suitable for use in dry powder inhalers with additive material which becomes attached to the surfaces of the carrier particles.

Additive material, which may be in liquid form or may comprise additive particles, or agglomerates of additive particles, may be introduced to a sample of carrier particles, which may have been treated as described below, and the mixture blended to allow the additive material to become attached to the surfaces of the carrier particles.

As indicated above, the exact ratio in which the carrier particles and the additive particles are mixed will, of course, depend on the type of device and the type of active particles used. Also as indicated above, the proportion of the additive material in the powder is of particular importance.

The size of the carrier particles is an important factor in the efficiency of the inhaler, and an optimum, or near optimum, range of size of particles is preferably selected. Therefore, the method advantageously further includes the step of selecting from a sample of carrier particles an advantageous range of size of carrier particles prior to the mixing step and, in the case where the additive material is in the form of particles when it is mixed with the carrier particles, preferably also includes the step of selecting from a sample of additive particles an advantageous range of size of additive particles prior to the mixing step. The step of selecting an advantageous range of size may be a sieving step.

Advantageously the additive material and the carrier particles are mixed for between 0.1 hours and 0.5 hours. The particles may be mixed using a tumbling blender (for example a Turbula Mixer).

Advantageously, the method further includes the step of treating the carrier particles to dislodge small grains from the surfaces of the carrier particles, without substantially changing the size of the carrier particles during the treatment.

As indicated above, the surface of a carrier particle is not usually smooth but has asperities and clefts in the surface. As a result, the surfaces have areas of high surface energy to which active particles are preferentially attached. An active particle at a high energy site is less likely to be able to leave the surface and be dispersed in the respiratory tract than an active particle at a site of lower surface energy. During the treatment referred to immediately above, asperities are removed as small grains, thus removing active sites associated with the asperities.

Advantageously, the mixing step is prior to the treatment step. The additive material may therefore be added in the form of large particles which are broken into smaller particles during the treatment. Alternatively the treatment may be carried out before the addition of the additive material or, alternatively, after the addition of the additive material and of the active particles.

Advantageously, the small grains become reattached to the surfaces of the carrier particles. The object of treating the carrier particles is to reduce the number of high energy sites on the carrier particle surfaces, thus allowing an even deposition of active particles adhered on the surface with a force of adhesion such that dispersion of the active particles during inhalation is efficient. While removing asperities as small grains removes those high energy sites associated with the asperities, the surfaces of the carrier particle have other high energy sites, for example at the site of clefts, which sites are not necessarily removed when the asperities are removed. It is highly advantageous to decrease the number of high energy sites.

The grains removed from the surface are small and thermodynamically unstable and are attracted to and adhere to the remaining high energy sites on the surface of the carrier particles. Furthermore, where the additive material is in the form of particles, the additive particles are attracted to the high energy sites which therefore can become saturated. That situation is highly preferable as is described above. On introduction of the active particles, many of the high energy sites are already occupied, and the active particles therefore occupy the lower energy sites on the carrier particle surface, or on the surface of the additive particles. That results in the more efficient release of the active particles in the airstream created on inhalation, thereby giving increased deposition of the active particles in the lungs.

It will be understood that the term "carrier particles" refers to the particles on which the small grains become attached. References to carrier particles above, for example in respect of particle size, do not therefore include those small grains.

Advantageously, the treatment step is a milling step. The milling causes asperities on the surfaces of the carrier particles to be dislodged as small grains. Many of those small grains become reattached to the surfaces of the carrier particles at areas of high energy as described above.

Preferably, the milling step is performed in a ball mill. The particles may be milled using plastics balls, or they may be milled using metal balls. Balls made of polypropylene material give less aggressive milling, whilst steel balls confer more aggressive action. The mill may be rotated at a speed of about 60 revolutions per minute. The mill may alternatively be rotated at a speed less than 60 revolutions per minute, for example at a speed of less than about 20 revolutions per minute, or for example a speed of about six revolutions per minute. That is a slow speed for ball milling and results in the gentle removal of grains from the surfaces of the particles and little fracture of the particles. Widespread fracture of the particles, which occurs with aggressive milling conditions, or at long milling times, may result in agglomerates of fractured particles of carrier material.

Advantageously, the particles are milled for at least 0.25 hours, preferably the particles are milled for not longer than about 6 hours. That time has been found to be suitable when milling with balls made from plastics material. When using denser balls, or alternative materials, shorter milling times may be used. Alternatively, a different milling technique may be used, for example using a re-circulated low fluid energy mill, or other method that results in the removal of grains from the surfaces of the particles, for example sieving, or cyclone treatment.

As indicated above, the size of the particles is important and the method may further include the step of selecting an advantageous range of size of particles prior to the treatment step.

Where reference is made to the size of the carrier particles being substantially unchanged during the treatment, it will of course be understood that there will be some change in the size of the carrier particles because portions of the particle are removed as small grains during the treatment. However, that change in size will not be as large as that obtained when particles are milled in a conventional more aggressive way. The gentle milling used in the treatment is referred to as "corrasion".

According to the invention, there is further provided a method of producing a powder for use in dry powder inhalers, the method including the steps of (a) mixing carrier particles of a size suitable for use in dry powder inhalers with additive material such that the additive material becomes attached to the surfaces of the carrier particles.

(b) treating the carrier particles to dislodge small grains from the surfaces of the carrier particles, without substantially changing the size of the carrier particles during the treatment and (c) mixing the treated particles obtained in step (b) with active particles such that active particles adhere to the surfaces of the carrier particles and/or the additive material.

A satisfactory dry powder may also be obtained by mixing the active particles, the additive material and the carrier particles together in one step. Alternatively, the carrier particles may first be mixed with the active particles, followed by mixing with the additive material.

Satisfactory dry powders may also be obtained by an alternative sequence of steps. For example, the carrier particles, additive material and active particles may be mixed together followed by a milling step. Alternatively, the carrier particles may first be milled before the addition of additive material and active particles.

The invention also provides a method of producing a powder for use in dry powder inhalers, the method including the steps of producing particles as described above and mixing the particles with active particles such that active particles adhere to the surfaces of the carrier particles and/or additive material.

According to the invention, there is also provided the use of additive material attached to the surfaces of carrier particles for carrying active particles in a powder for use in a dry powder inhaler, for the promotion of the release of active particles from the surfaces of carrier particles during inhalation, the powder being such that the active particles are not liable to be released from the carrier particles before actuation of the inhaler.

Embodiments of the invention will now be described by way of example with reference to the accompanying drawings, of which:

FIG. 1 shows a section through a carrier particle including additive particles on its surfaces;

FIG. 2 is a perspective view of a dry powder inhaler;

FIG. 3 is a sectional diagram of a twin stage impinger; and

FIGS. 4*a* & 4*b* show the effect of a milling treatment on the carrier particle of FIG. 1.

EXAMPLE 1

Carrier particles were prepared by the following method. Meggle lactose EP D30 (an α lactose monohydrate: pure crystalline milk sugar) was used. Lactose EP D30 has a useful particle size range and acceptable flow properties.

(a) The lactose was sieved by the following method to give samples having particles with a range of diameter from 90 μm to 125 μm. Successive samples of about 500 g, of lactose were sieved mechanically for 40 minutes using successively woven wire stainless steel sieves of aperture diameters 63 μm, 90 μm and 125 μm. The mesh was vibrated at high speed on a Boulton rotary gyrator to reduce the binding of lactose particles to the mesh of the sieve. In order to try to improve the efficiency of the sieving process, after twenty minutes of the sieving process, the sieving was stopped and the sieve was removed and the powder on the sieve was removed, the sieve brushed and the powder replaced in the sieve from which it was removed. The sieve was then replaced and the sieving resumed.

200 g samples of the lactose EP D30 were taken from the particles which had passed through the 125 μm mesh sieve but had remained on the 90 μm sieve. Those particles could be considered to have a diameter between 90 μm and 125 μm.

(b) Samples of lactose particles obtained in step (a) above were treated by mixing the lactose particles with additive particles. 2 g of leucine (L-leucine α-aminoisocaproic acid) were added to 198 g of the lactose particles and mixed in a Turbula Mixer for approximately 15 minutes.

The leucine particles used were of a size such that 95% by weight of the particles had a diameter of less than 150 μm. The mixture obtained contained approximately 1% leucine by weight.

FIG. 1 shows a representation of a particle 1 having asperities 2 and clefts 3. The additive particles 4 have become attached to the surface of the particle, mostly at the active sites on the surface. As can be seen from FIG. 1, the additive particles 4 cover only parts of the surface of the particle, other parts of the surface remaining exposed.

(c) Samples of the particles including additive particles (obtained in step (b)) were mixed with active particles. 0.132 g of beclomethasone dipropionate (BDP) (mass median diameter 1.13 μm) were added to 29.868 g of the particles in a glass mortar. Each 30 g of mixture was blended.

The blending process with 0.132 g of BDP was repeated for a 29.868 g sample of lactose particles having a diameter between 90 μm and 125 μm (obtained in step (a)), but which had not been mixed with the additive particles, to give a comparative example.

(d) After one day, several samples each of 25 mg of mixture were taken from the container containing the particles including the additive particles and several samples each of 25 mg were taken from the container containing the particles which had not been mixed with the additive particles. Each sample was used to fill a respective one of a number of size three capsules (size 3 transparent capsules obtained from Davcaps of Hitchen, Herts., England). Those filled capsules were allowed to stand for one day to allow the decay of any accumulated electric charge.

(e) The effect of the mixing of the lactose particles with additive particles was verified using a dry powder inhaler device and a pharmacopoeial apparatus, for in vitro assessment of inhaler performance.

Figure 2:
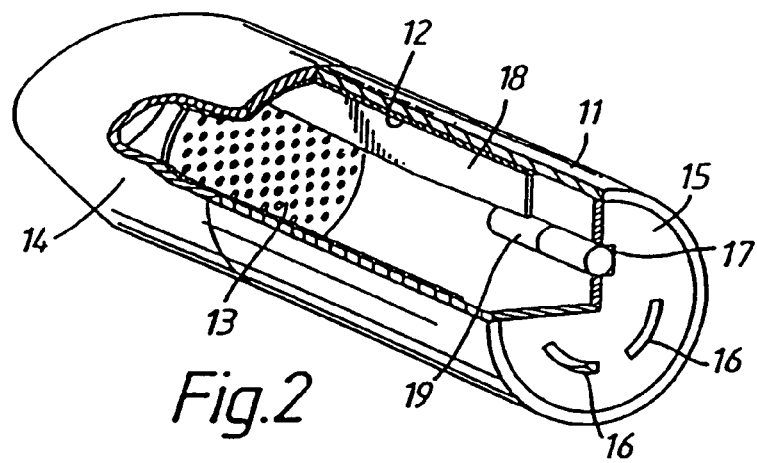

(e)(i) FIG. 2 shows a view of a dry powder inhaler known as a Rotahaler (trade mark of Glaxo). The inhaler comprises an outer cylindrical barrel 11 and an inner cylindrical barrel 12 of similar radius such that the inner barrel 12 is just able to fit inside the outer barrel 11. A mesh 13 is attached across an end of the inner barrel 12 and a mouthpiece 14 is attached around that end section of the inner barrel 12. The outer barrel 11 is closed at one end by an end section 15 which contains inlet slots 16 and an aperture 17. The inner barrel 12 also contains a fin 18 along a length of the inner barrel at the open end, the fin extending radially inwards from the internal surface of the inner barrel 12.

To operate the device, the inner barrel 12 is inserted into the open end of the outer barrel 11 such that the mouthpiece meets the outer barrel 11 and the open end of the inner barrel is at the end section 15. Capsule 19 containing the mixture of carrier particles and active particles is inserted into the aperture 17 such that a portion of the capsule 19 is held in the end section 15, and a portion of the capsule 19 extends into the inner barrel 12. The outer barrel 11 is rotated relative to the inner barrel 12 and thus the fin 18 engages and breaks the capsule. A patient inhales through the mouthpiece 14, air is drawn into the Rotahaler through the inlet slots 16, and the contents of the capsule are discharged into the inner barrel as a cloud of powder and inhaled via the mouthpiece 14. The mesh 13 prevents the inhalation of large particles or of the broken capsule.

Figure 3:
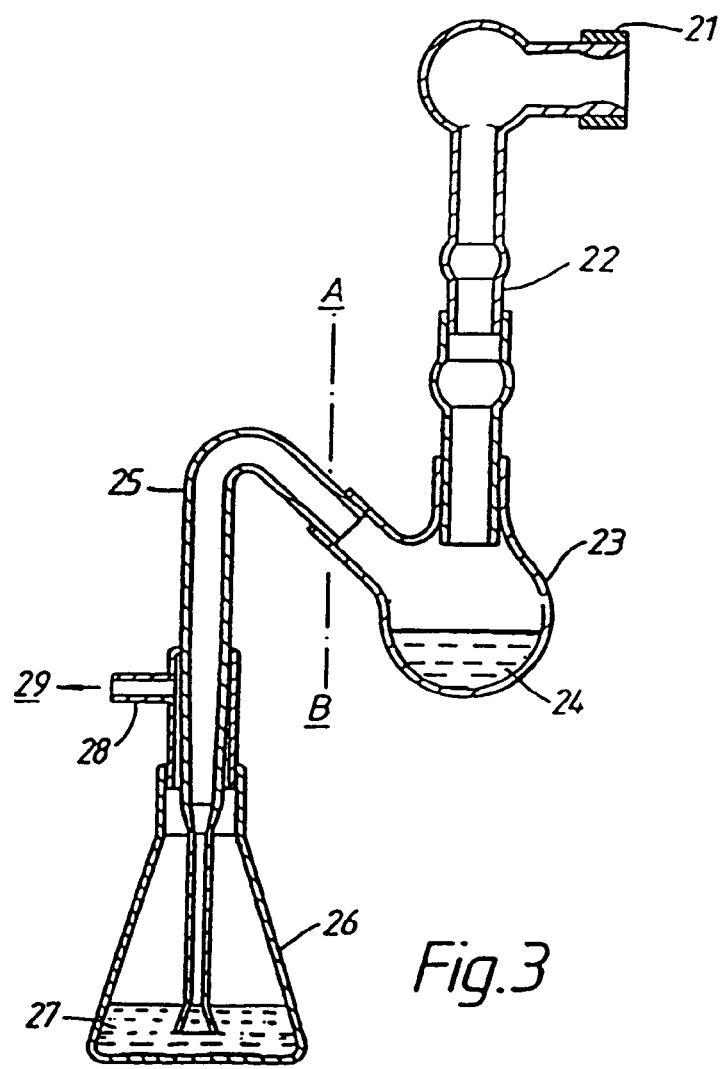

(e)(ii) FIG. 3. shows a diagrammatic arrangement of a twin stage impinger (TSI). The TSI is a two stage separation device used in the assessment of oral inhalation devices. Stage one of the apparatus is shown to the right of the line AB in FIG. 3 and is a simulation of the upper respiratory tract. To the left of that line is stage two which is a simulation of the lower respiratory tract.

The TSI comprises a mouth 21 which comprises a polydimethylsiloxane adaptor, moulded to accept the mouthpiece of the inhaler device, upper tubing 22 and upper impinger 23 to simulate the upper respiratory tract, the upper impinger containing liquid 24, and lower tubing 25 and lower impinger 26 to simulate the lower respiratory tract, the lower impinger containing liquid 27. The lower impinger 26 is connected via an outlet pipe 28 to a pump 29 which draws air through the TSI apparatus at a predetermined rate. The base of the lower tubing 25 is below the level of the liquid 27 such that all the air drawn through the TSI bubbles through the lower liquid 27. The liquid used in both the upper and lower impinger is a suitable solvent for the drug to be tested.

In use, the inhaler is placed in a mouth 21 of the TSI. Air is caused to flow through the apparatus by means of a pump 29 which is connected to stage two of the TSI. Air is sucked through the apparatus from the mouth 21, flows through upper tubing 22 via the upper impinger 23 and the lower tubing 25 to the lower impinger 26 where it bubbles through liquid 27 and exits the apparatus via outlet pipe 28. The liquid 24 in the upper impinger 23 traps any particle, with a size such that it is unable to reach stage two of the TSI. Fine particles, which are the particles able to penetrate to the lungs in the respiratory tract, are able to pass into stage two of the TSI where they flow into the lower impinger liquid 27.

(f) 30 ml of solvent was put into the lower impinger 26 and 7 ml of solvent was put into the upper impinger 23. The lower tubing 25 was arranged such that its lower end was below the level of the solvent in the lower impinger 26. The pump 29 was adjusted to give an air flow rate of 60 litres per minute in the apparatus.

The Rotahaler was weighed when empty. One of the prepared capsules was inserted into aperture 17 and the inhaler was reweighed. The mouthpiece 14 of the inhaler was connected to the mouth 21 of the TSI, the outer barrel 11 was rotated to break the capsule 19 and the pump was switched on and timed for a period of ten seconds. The pump was then switched off and the Rotahaler was removed from the TSI, reweighed and the amount of powder lost from the inhaler calculated.

The remaining powder in the inhaler was washed into a flask for analysis and made up to 25 ml with solvent. The sections of the apparatus making up stage one of the TSI were washed into a second flask and made up to 50 ml with solvent. The sections making up the second stage of the TSI were washed into a third flask and made up to 50 ml with solvent.

The other capsules were tested in the same way in a predetermined random order.

The contents of the flasks containing the washing from the stages of the TSI were assayed using High Performance Liquid Chromatography (HPLC) analysis for the content of BDP and compared against standard solutions containing 0.5 µg/ml and 1 µg/ml of BDP.

The percentage of BDP in each stage of TSI was calculated from the standard response for each capsule and the mean for the treated samples and the untreated samples could be calculated.

(g) Table 1 below shows the BDP content (in µg) recovered from each stage of the TSI as an average for the samples of the treated and the untreated material. The respirable fraction (calculated as the percentage of the total amount of drug emitted from the device, that reaches stage two of the TSI) gives an indication of the proportion of active particles which would reach the deep lung in a patient. The numbers in brackets indicate the coefficient of variation for each value.

TABLE 1

|  | no additive particles added | 1% leucine added |
|---|---|---|
| Device | 11.3 (19.7) | 26.8 (6.8) |
| Stage 1 | 88.0 (4.7) | 63.6 (3.1) |
| Stage 2 | 1.3 (40.5) | 7.5 (9.0) |
| Respirable Fraction (%) | 1.4 (37.5) | 10.5 (6.8) |

The results show that there has been an increase in the deposition of active particles in Stage two of the TSI: indicating an increased deposition in the deep lung for the samples containing leucine.

In addition, the coefficient of variation for each value for the treated samples was reduced: indicating increased reproducibility of the results (corresponding to improved dose uniformity of the administered drug).

EXAMPLE 2

(a) Samples of lactose particles having particles with a range of diameter from 90 μm to 125 μm were prepared as in Example 1 (a) above.

(b) Samples of lactose particles obtained in step (a) were treated by mixing the lactose particles with additive particles.

4 g of leucine (having 95% of weight of particles having a diameter less than 150 μm) were added to 196 g of lactose particles and blended as described in Example 1 (b). The mixture obtained contained approximately 2% leucine by weight.

(c) Samples of the particles obtained in step (b) including the additive particles were mixed with active particles as described above for Example 1 (c) and the samples were analysed as described in steps (d) to (f) for Example 1.

(d) Table 2 below shows the BDP content (in μg) recovered from each stage of the TSI as an average for the samples including the additive particles, and the respirable fraction. The figures for the samples from Example 1 to which no additive particles were added are shown for comparison.

TABLE 2

| | no additive particles added | 2% leucine added |
|---|---|---|
| Device | 11.3 (19.7) | 24.2 (7.0) |
| Stage 1 | 88.0 (4.7) | 61.9 (2.0) |
| Stage 2 | 1.3 (40.5) | 6.2 (14.9) |
| Respirable Fraction (%) | 1.4 (37.5) | 9.0 (11.9) |

EXAMPLE 3

(a) Samples of carrier particles comprising lactose and 1% by weight leucine particles were prepared as described in steps (a) and (b) of Example 1.

(b) Several samples of the carrier particles were each milled in a porcelain ball mill (Pascall Engineering Company) with 1200 ml of 20 mm plastics balls.

Samples (A), of which there were several, were milled at 60 rpm for three hours.

Samples (B) were milled at 60 rpm for six hours.

Samples (C) and (D) were milled at 40 rpm for two hours and four hours respectively.

(c) The samples were mixed with active particles as described in Example 1 (c) for the particles including the additive particles and analysed as described in steps (d) to (f) for Example 1.

(d) Table 3 below shows the BDP content (in μg) recovered from each stage of the TSI as an average for the milled samples (A) to (B), and the respirable fraction. The figures for the unmilled (1% leucine added) samples from Example 1 are shown for comparison.

The results show that there has been a significant increase in the respirable fraction, indicating increased deposition in the deep lung for the milled samples.

TABLE 3

| | lactose with 1% leucine and BDP | | | | |
|---|---|---|---|---|---|
| | unmilled | (A) | (B) | (C) | (D) |
| Device | 26.8 (6.8) | 32.1 (9.9) | 36.1 (12.8) | 33.7 (10.1) | 36.2 (7.2) |
| Stage 1 | 63.6 (3.1) | 48.8 (7.2) | 35.7 (6.7) | 52.5 (4.8) | 41.2 (4.5) |
| Stage 2 | 7.5 (9.0) | 21.8 (14.9) | 30.8 (7.6) | 13.6 (10.6) | 22.1 (16.9) |
| Respirable fraction (%) | 10.5 (6.8) | 30.8 (11.2) | 46.3 (4.7) | 20.5 (6.5) | 34.8 (10.5) |

FIGS. 4*a* and 4*b* show the effect of the milling step. The shaded areas 5 of the particle 1 represent the sections removed from the surface of the particle as small grains during the milling. As shown in FIG. 4*b*, small grains 6 have become reattached to the surface of the particle, mostly at active sites.

The effect on the flow characteristics of the milled particles of the presence of leucine was investigated.

The Carr's index was measured for lactose (diameter 90 μm to 125 μm) samples (X), (Y) and (Z) where:

(X) contained milled lactose particles (Y) contained lactose particles to which 1% leucine had been added before milling (Z) contained milled lactose particles to which 1% leucine had been added.

In each case, the milling was performed in a porcelain ball mill with 1200 ml of 20 mm plastics balls. The mill was revolved at 60 rpm for six hours.

Carr's index for a weight (W) of each sample was determined by measuring the volume ($V_{loose}$) of weight (W) poured into a 250 cm³ measuring cylinder and tapping the cylinder to obtain constant volume of the sample ($V_{tap}$). The loose density and the tap density are calculated as $W/V_{loose}$ and $W/V_{tap}$ respectively and Carr's index is calculated from the tapped density and the loose density by the formula $$\text{Carr's Index (\%)} = \frac{\text{Tapped} - \text{loose}}{\text{Tapped}} \times 100$$

The Carr's index determined for each sample is given in table 4 below. A Carr's index of less than 25 is usually taken to indicate good flow characteristics; a Carr's index greater than 40 indicates poor flow characteristics.

TABLE 4

| Sample | Carr's index |
| --- | --- |
| X | 36.4 |
| Y | 32.1 |
| Z | 35.6 |

The results indicate that the flow characteristics were improved by the addition of leucine before milling (i.e. better flow).

EXAMPLE 4

(a) Samples of lactose having particles with a range of diameter from 90 μm to 125 μm were prepared as in Example 1 (a) above.

(b) Samples of lactose particles obtained in (a) were treated by mixing the lactose particles with additive particles.

1 g of soya lecithin particles were added to 199 g of the lactose particles and blended in a Turbula Mixer for 15 minutes. The mixture obtained contained approximately 0.5% soya lecithin by weight.

(c) Several samples of the particles prepared in step 4 (b) above were each milled in a porcelain ball mill (Pascall Engineering Company) with 1200 ml of 20 mm plastics balls. The samples were each milled at 60 rpm for six hours.

(d) The milled samples obtained in step 4 (c) above and the unmilled samples obtained in step 4 (b) above were each mixed with active particles as described in Example 1 (c) for the treated particles and analysed as described in steps (d) to (f) for Example 1.

(e) Table 5 below shows the BDP content (in μg) recovered from each stage of the TSI as an average for the milled samples and for the unmilled samples, and the respirable fraction.

TABLE 5

| | lactose with 0.5% soya lecithin and BDP | |
| --- | --- | --- |
| | unmilled | milled |
| Device | 22.9 (10.1) | 29.5 (10.7) |
| Stage 1 | 71.9 (3.5) | 45.2 (12.5) |
| Stage 2 | 3.4 (11.4) | 24.5 (11.1) |
| Respirable fraction (%) | 4.4 (8.4) | 35.3 (14.5) |

The results show a significant increase in the respirable fraction, indicating increased deposition in the deep lung, for the milled samples.

EXAMPLE 5

(a) Samples of lactose having particles within a range of diameter from 90 μm to 125 μm were prepared as in Example 1 (a) above.

(b) Samples of lactose particles obtained in (a) were treated by mixing the lactose particles with additive particles.

2 g of Aspartame particles were added to 198 g of the lactose particles and blended in a Turbula Mixer for 15 minutes. The mixture obtained contained approximately 1% aspartame by weight.

(c) Several samples of the particles prepared in step 5 (b) above were each milled in a porcelain ball mill (Pascall Engineering Company) with 1200 ml of 20 mm plastics balls. The samples were each milled at 60 rpm for six hours.

(d) The milled samples obtained in step 5 (c) above and the unmilled samples obtained in step 5 (b) above were each mixed with active particles as described in Example 1 (c) for the particles including the additive and analysed as described in steps (d) to (f) for Example 1.

(e) Table 6 below shows the BDP content (in μg) recovered from each stage of the TSI as an average for the milled samples and for the unmilled samples, and the respirable fraction.

TABLE 6

| | lactose with 1% aspartame and BDP | |
| --- | --- | --- |
| | unmilled | milled |
| Device | 29.1 (16.0) | 36.5 (10.7) |
| Stage 1 | 67.0 (8.2) | 41.4 (10.9) |
| Stage 2 | 4.6 (20.6) | 19.8 (5.2) |
| Respirable fraction (%) | 6.4 (13.6) | 32.4 (6.1) |

The results show a significant increase in the respirable fraction, indicating increased deposition in the deep lung for the milled samples.

EXAMPLE 6

(a) Samples of lactose having particles within a range of diameter from 90 to 125 μm were prepared as in Example 1 (a) above.

(b) Samples of lactose particles obtained in 6 (a) were treated by adding additive particles to the lactose particles and milling the lactose-additive particle mixture.

Five different sets of samples containing five different amino acids as additive materials were each prepared as follows:

2 g of additive particles were added to 198 g of the lactose particles (obtained in 6 (a)) in a 2.5 l porcelain pot containing 1200 ml of 20 mm plastic balls. The pot was placed on a ball mill (Pascall Engineering Company) and milled at 60 rpm for six hours.

The five amino acids were Leucine, Lysine, Methionine, Phenylalanine and Valine.

(c) The milled particles obtained in 6 (b) were mixed with active particles. 0.132 g of beclomethasone dipropionate (BDP) were added to 29.868 g of the particles in a glass mortar. Each 30 g mixture was blended.

(d) The powder samples obtained in 6 (c) were analysed using the TSI as described in steps (d) to (f) for Example 1.

(e) Table 7 below shows the BDP content (in μg) recovered from each stage of the TSI as an average for the samples for each of the five different additive materials, and the respirable fraction. For comparison, a control formulation, prepared as described in steps (a) to (c) above but not including any additive material, was also analysed as in step (d) above.

TABLE 7

|  | Control | Leucine | Lysine | Methi-onine | Phenylaline | Valine |
|---|---|---|---|---|---|---|
| Device | 33.0 | 36.1 | 33.9 | 31.5 | 31.0 | 40.8 |
| Stage 1 | 51.1 | 35.7 | 52.1 | 45.1 | 46.7 | 46.9 |
| Stage 2 | 17.5 | 30.8 | 23.6 | 25.6 | 23.8 | 19.6 |
| Respirable Fraction (%) | 25.5 (11.0) | 46.3 (4.7) | 31.0 (11.6) | 36.2 (1.7) | 33.8 (5.6) | 29.5 (7.7) |

EXAMPLE 7

(a) Samples of lactose having particles within a range of diameter from 90 to 125 μm were prepared as in Example 1 (a) above.

(b) Samples of lactose particles obtained in 7 (a) were treated by adding particles of aspartame to the lactose particles and milling the mixture as follows:

2 g of aspartame particles were added to 198 g of the lactose particles (obtained in 7 (a)) in a 2.5 l porcelain pot containing 1200 ml of 20 mm plastics balls. The pot was placed on a ball mill (Pascall Engineering Company) and milled at 60 rpm for six hours.

(c) The milled particles obtained in 7 (b) were mixed with active particles as described in step (c) of Example 6.

(d) The powder samples obtained were analysed using the TSI as described in steps (d) to (f) of Example 1.

(e) Table 8 below shows the BDP content (in μg) recovered from each stage of the TSI as an average for the samples, and the respirable fraction. The results of the control (as in Example 6) are shown for comparison.

TABLE 8

|  | Control | Aspartame added |
|---|---|---|
| Device | 33.0 | 36.5 |
| Stage 1 | 51.1 | 41.4 |
| Stage 2 | 17.5 | 19.8 |
| Respirable Fraction (%) | 25.5 (11.0) | 32.4 (6.1) |

EXAMPLE 8

(a) Samples of lactose having particles within a range of diameter from 90 to 125 μm were prepared as in Example 1 (a) above.

(b) Samples of lactose particles obtained in 8 (a) were treated by adding particles of soya lecithin to the lactose particles and milling the mixture as follows:

1 g of soya lecithin was added to 199 g of the lactose particles (obtained in 8 (a)) in a 2.5 l porcelain pot containing 1200 ml of 20 mm plastics balls. The pot was placed on a ball mill (Pascall Engineering Company) and milled at 60 rpm for six hours.

(c) The milled particles obtained in 8 (b) were mixed with BDP as described in step (c) of Example 6.

(d) The powder samples obtained were analysed using the TSI as described in steps (d) to (f) of Example 1.

(e) Table 9 below shows the BDP content (in μg) recovered from each stage of the TSI as an average for the samples, and the respirable fraction. The results of the control (as in Example 6) are shown for comparison.

TABLE 9

|  | Control | Lecithin added |
|---|---|---|
| Device | 33.0 | 44.8 |
| Stage 1 | 51.1 | 37.5 |
| Stage 2 | 17.5 | 23.4 |
| Respirable Fraction (%) | 25.5 (11.0) | 38.3 (4.3) |

EXAMPLE 9

(a) Samples of lactose having particles within a range of diameters from 90 to 125 μm were prepared as in Example 1 (a) above.

(b) Samples of lactose particles obtained in 9 (a) were treated by milling a mixture of the lactose particles and particles of wheat starch. Milled samples of lactose and starch particles were prepared as follows:

1 g of particles of wheat starch were added to 199 g of the lactose particles in a 2.5 l porcelain pot containing 1200 ml of 20 mm plastics balls. The pot was then placed on a ball mill (Pascall Engineering Company) and milled at 60 rpm for six hours.

(c) The milled particles obtained in 9 (b) were mixed with active particles. 0.264 g of salbutamol sulphate (SBS) were added to 29.736 g of the particles in a glass mortar. Each 30 g mixture was blended.

(d) The powder samples obtained in 9 (c) were then analysed as described in steps (d) to (f) of Example 1 but with the stages of the TSI being analysed for the SBS content.

Table 10 below shows the SBS content (in μg) recovered from the device and from each stage of the TSI as an average for the samples.

The respirable fraction (RF) is also shown and the number in brackets indicates the coefficient of variation of the value.

TABLE 10

|  | Wheat starch |
|---|---|
| Device | 94.7 |
| Stage 1 | 89.1 |
| Stage 2 | 60.9 |
| RF (%) | 40.8 (12.8) |

EXAMPLE 10

(a) Samples of lactose having particles with a range of diameter from 90 μm to 125 μm were prepared as in Example 1 (a) above.

(b) Additive material was added to the lactose particles as follows:

1 g of soya lecithin (90% by weight of particles less than 710 μm) was dissolved in 10 g water and 10 g 1 MS (or in 20 g 95% ethanol) and added to 199 g of the lactose particles in a high shear mixer.

The resulting mixture was blended for four minutes and then dried on trays at 40° C. for 6 hours. The powder was screened through a 500 μm sieve.

The powder samples obtained contained approximately 0.5% soya lecithin by weight.

(c) The samples obtained in step 10 (b) above were each mixed with active particles as described in Example 1 (c) for the treated particles and analysed as described in steps (d) to (f) for Example 1.

(d) Table 11 below shows the BDP content (in μg) recovered from each stage of the TSI as an average for the samples, and the respirable fraction.

TABLE 11

|  | no additive material added | 0.5% soya lecithin added |
|---|---|---|
| Device | 11.3 (19.7) | 22.9 (10.1) |
| Stage 1 | 88.0 (4.7) | 71.9 (3.5) |
| Stage 2 | 1.3 (40.5) | 3.4 (11.4) |
| Respirable fraction (%) | 1.4 (37.5) | 4.4 (8.4) |

The results show that there has been an increase in the deposition of active particles in Stage two of the TSI indicating an increased deposition in the deep lung for the samples containing soya lecithin.

EXAMPLE 11

Samples of milled lactose including leucine as additive material were prepared and tested using the TSI to investigate the effect of using different dry powder inhaler devices and different drugs.

(i) The milled samples of lactose and leucine were prepared as follows:

(a) Samples of lactose having particles within a range of diameter from 90 to 125 μm were prepared as in Example 1 (a) above.

(b) Samples of lactose particles obtained in 11 (a) were treated by adding leucine particles to the lactose particles and milling the mixture.

2 g of leucine particles were added to 198 g of the lactose particles in a 2.5 l pot which also contained 1200 ml of 20 mm plastics balls. The pot was then placed on a ball mill (Pascall Engineering Company) and milled at 60 rpm for six hours.

(ii) Several samples of the particles obtained in (i) were each mixed with active particles as described below.

(a) 0.132 g of BDP were added to 29.868 g of the particles in a glass mortar and the mixture was blended.

(b) 0.132 g of SBS were added to 29.868 g of the particles in a glass mortar and the mixture was blended.

(c) 0.264 g of budesonide (BSN) were added to 29.736 g of the particles in a glass mortar and the mixture was blended.

(iii) The powders obtained in (ii) were analysed using the TSI with three different inhaler devices.

(a) Rotahaler (trade mark of Glaxo). The powder was analysed as described in steps (d) to (f) for Example 1.

(b) Diskhaler (trade mark of Glaxo)

Several samples of the powder, each of 25 mg, were taken from the container. Each sample was used to fill a blister pocket in a package of commercial Becodisks (trade mark of Glaxo), from which the commercial formulation had been removed. The refilled blister packages were allowed to stand for one day to allow the decay of any accumulated electrostatic charge. To evaluate the performance of the powder in the Diskhaler, the blister package was inserted into the Diskhaler and the mouthpiece of the inhaler was connected to the mouthpiece of the TSI. The analysis performed was analogous to that described in steps e(ii) to (f) for Example 1.

(c) Cyclohaler (manufactured by Pharbita B.V.) The method of analysing the powders was analogous to that described in steps (d) to (f) for Example 1.

(iv) The analysis was repeated for each inhaler device using the commercially available preparations of the active materials BDP, SBS and BSN (those preparations not containing the additive material and having not been treated as the powders tested in (iii)). For the Rotahaler there was no commercial formulation of BSN available. A formulation was prepared for comparison by preparing the powder as described above without adding the leucine.

Table 12 below shows the active material (BDP, SBS, BSN) content (in μg) for the device and stages 1 and 2 of the TSI and the respirable fraction. The results shown are the average of the replicate tests performed. The figures in brackets show the coefficient of variation. The results shown are in respect of the three different inhaler devices: Rotahaler (RH), Diskhaler (DH) and Cyclohaler (CH) for both the commercial formulation (C) and the powder containing leucine as additive (L).

TABLE 12

| Inhaler | Active Component | Formulation | Device | Stage 1 | Stage 2 | Respirable Fraction |
|---|---|---|---|---|---|---|
| RH | BDP | C | 25.6 | 64.0 | 14.9 | 14.9 (15.7) |
| RH | BDP | L | 36.1 | 35.7 | 30.8 | 46.3 (4.7) |
| DH | BDP | C | — | 67.8 | 17.8 | 20.8 (5.1) |
| DH | BDP | L | — | 50.0 | 38.9 | 44.0 (7.7) |
| RH | SBS | C | 60.1 | 110.0 | 40.3 | 26.8 (13.4) |
| RH | SBS | L | 99.0 | 47.9 | 60.0 | 55.7 (9.0) |
| DH | SBS | C | — | 114.9 | 74.7 | 39.4 (7.9) |
| DH | SBS | L | — | 84.9 | 126.6 | 59.9 (4.3) |
| CH | SBS | C | 49.2 | 170.8 | 36.0 | 17.4 (11.9) |
| CH | SBS | L | 63.3 | 48.7 | 74.6 | 60.6 (4.7) |
| RH | BSN | No leucine | 47.7 | 46.9 | 16.5 | 26.0 (5.5) |
| RH | BSN | L | 33.7 | 35.4 | 27.8 | 44.3 (10.2) |

EXAMPLE 12

Samples of milled lactose including L-leucine as additive material at different concentrations were prepared and tested using the TSI to investigate the effect of using different amounts of leucine.

(a) Samples of lactose having particles within a range of diameters from 90-125 μm were prepared as in Example 1 (a) above.

(b) Samples of lactose particles obtained in (a) were treated by milling (corrading) the lactose particles with additive particles of L-leucine.

Appropriate weights of additive particles were added to appropriate weights of the lactose particles in a 2.5 l porcelain pot, which also contained 200 ml of 3 mm steel balls. The pot was in each case then placed on a ball mill (Pascall Engineering Company) and milled at 60 r.p.m. for 6 hours.

The weights of L-leucine (additive particles) and lactose particles in the various samples were as detailed in Table 13 below:

TABLE 13

| Weight of additive particles | Weight of lactose particles | % Concentration of additive particles |
|---|---|---|
| 2 g | 198 g | 1.0% |
| 4 g | 196 g | 2.0% |
| 12 g | 188 g | 6.0% |

Several samples of each concentration were prepared.

Once the samples had been milled for the full 6 hours, the pots were opened and the powders qualitatively assessed for evidence of caking.

Caking is the appearance of non-redispersible material around the edges of the pot and indicates poor processibility. It was noted that the extent of caking markedly increased as the L-leucine concentration increased from 1 to 6% Indeed, at a level of 6% L-leucine an extremely high level of caking was observed, indicating that this mix could not be effectively processed on a commercial scale.

(c) The milled samples obtained in (b) were then mixed with active particles of BDP as described in Example 1 (c).

(d) The milled samples mixed with the active particles obtained in (c) were then analysed as described in steps (d) to (f) for Example 1.

Table 14 below shows the BDP content (in μg) recovered from the device and from each stage of the TSI as an average of the replicate experiments. The respirable fractions are also shown, and the figures in parenthesis denote the coefficients of variation. The results from a control formulation, prepared as described above but without any leucine particles are also shown.

TABLE 14

| | | % Concentration of leucine | | |
|---|---|---|---|---|
| | Control | 1% | 2% | 6% |
| Device | 28.9<br>(36.2) | 32.9<br>(12.6) | 28.8<br>(9.3) | 27.6<br>(2.7) |
| Stage 1 | 58.5<br>(13.0) | 35.2<br>(9.95) | 27.9<br>(5.8) | 33.2<br>(8.2) |
| Stage 2 | 15.5<br>(17.1) | 33.7<br>(5.1) | 43.3<br>(2.9) | 42.5<br>(6.7) |
| Respirable fraction (%) | 20.9<br>(11.5) | 49.0<br>(4.8) | 60.8<br>(2.4) | 56.2<br>(6.4) |

From the results shown above, it can be seen that no increase in respirable fraction is obtained from increasing the concentration of leucine above about 2 per cent. Increasing the concentration above about 2 per cent does however adversely affect the ability to process the mix making it more difficult to process and at concentrations above 5 per cent of leucine the mix becomes very much more difficult to process.

It is possible to make a quantitative assessment of the tendency of any particular powder to segregate. The following procedure can be adopted:

Thirteen interlocking plastic cylinders (internal diameter and height each approximately 1 cm) are assembled into a tower. The tower is then carefully filled with a sample of the dry powder formulation for testing to produce a stack of powder approximately 13 cm high. The initial homogeneity of the powder is then assessed by removing two, approximately 25 mg, samples of powder (noting the exact weights with an analytical balance) from different points on the top surface of the uppermost cylinder. The uppermost cylinder is then removed from the stack by sliding it sideways. This procedure is then repeated until two samples have been taken from each of the first ten cylinders in the original stack.

The drug content of each powder sample is then determined using the same HPLC analysis as employed for the TSI experiments, as described in Example 1 (f).

In order to determine the initial homogeneity, the quantity of drug (as determined by HPLC) in each sample is expressed as a percentage of the original recorded weight of the powder sample. The values for all the samples are then averaged to produce a mean value, and the coefficient of variation (Cv) around this mean calculated. The coefficient of variation is a direct measure of the homogeneity of the mix.

The following procedure is then used to simulate the effects of pharmaceutical processing conditions on the homogeneity of the dry powder formulations.

The cylinder tower, filled with dry powder formulation as described above, is attached to an electronic vibration unit. The instrument is set to a frequency of 50 Hz, with a vibrational amplitude of 2 g, and is switched on to vibrate the cylinder containing the test powder vertically for 15 minutes. The purpose of the vibration is to subject the powder to treatment comparable to that which it might experience during commercial processing. The homogeneity of the dry powder formulation is then assessed using substantially the procedure described above. The vibrations will cause the powder to compact, with the result that, for example, the three uppermost cylinders may not contain any powder at the end of the vibration. Such cylinders are not included in the statistical analysis.

A powder, whose post-vibration homogeneity measured as a percentage coefficient of variation, is less than about 5% can be regarded as acceptable and a coefficient of variation of 2% is excellent.

EXAMPLE 13

Samples of powder including L-leucine and magnesium stearate as additive materials were prepared and the tendency of the powders to segregate quantitatively assessed. The details of the procedure adopted were as follows:

(a) Samples of lactose having particles within a range of diameters from 90-125 μm were prepared as in Example 1 (a) above.

(b) Samples of lactose particles obtained in (a) were treated by milling (corrading) the lactose particles with additive particles of a ternary agent. The additive particles consisted of either L-leucine or magnesium stearate.

Appropriate weights of additive particles were added to appropriate weights of the lactose particles in a 2.51 porcelain pot, which also contained 200 ml of 3 mm steel balls. The pot was in each case then placed on a ball mill (Pascall Engineering Company) and milled at 60 r.p.m for 6 hours.

The weights and types of additive particles and the weights of the lactose particles in the various tests were as detailed in Table 15 below:

TABLE 15

| Type of additive particles | Weight of additive particles | Weight of lactose particles (g) | Concentration of additive particles |
|---|---|---|---|
| Magnesium stearate | 3 g | 197 g | 1.5% |

TABLE 15-continued

| Type of additive particles | Weight of additive particles | Weight of lactose particles (g) | Concentration of additive particles |
|---|---|---|---|
| L-leucine | 2 g | 198 g | 1.0% |
| L-leucine | 4 g | 196 g | 2.0% |

(c) The milled samples obtained in (b) were then mixed with active particles of BDP as described in Example 1 (c).

(d) The powders obtained from step (c) were then subjected to the segregation test described above employing a tower of plastic cylinders. For each powder a first test was carried out without vibration to enable an initial homogeneity, expressed as a percentage coefficient of variation, to be determined; and a second test was carried out after vibration to enable a post-vibration homogeneity, expressed again as a percentage coefficient of variation, to be determined. For the second test, it was found that the top three cylinders were substantially empty after vibration and therefore no results for those cylinders were included in the statistical analysis.

The results of the tests are shown in Table 16 below:

TABLE 16

| Additive particles | Initial homogeneity (% CV) | Post-vibration homogeneity (% CV) |
|---|---|---|
| 1.5% Magnesium stearate | 8.73 | 15.26 |
| 1.0% L-leucine | 1.40 | 4.07 |
| 2.0% L-leucine | 1.71 | 2.07 |

The poor initial homogeneity of the 1.5% magnesium stearate mix indicates the very strong tendency of the mix to segregate. The post-vibration results confirm the poor stability of the mix when subjected to conditions comparable to those that might occur during commercial processing. Thus, even though a 1.5% magnesium stearate mix may provide satisfactory results in terms of a respirable fraction, it does not meet the other important requirement of retaining homogeneity during conditions that are comparable to those that might occur during commercial processing. In contrast the powders containing leucine, as well as providing a satisfactory respirable fraction, had excellent initial homogeneities and the homogeneities remained satisfactory even after intense vibration.

The invention claimed is:

1. A method of preparing a powder for use in a dry powder inhaler, the powder comprising active particles, carrier particles for carrying active particles, and particles of additive material; said method comprising:

(a) mixing carrier particles of a size suitable for use in dry powder inhalers with particles of additive material, so that the particles of additive material become attached to the surfaces of the carrier particles; and then (b) mixing active particles with the carrier particles and additive material from step (a), so that the active particles adhere to the surfaces of the carrier particles and/or additive material;

wherein the additive material is a physiologically acceptable material and promotes the release of the active particles from the carrier particles on actuation of the inhaler, wherein some of the particles of additive material may act as carriers of active particles and may be separate from or may separate from the surfaces of the carrier particles with active particles attached to their surfaces, and wherein the powder has a post-vibration homogeneity measured as a percentage coefficient of variation of less than about 5%.

2. A method as claimed in claim 1, wherein the method further includes the step of selecting from a sample of carrier particles an advantageous range of size of carrier particles prior to the mixing step (a).

3. A method as claimed in claim 1, wherein the method further includes the step of selecting from a sample of additive particles an advantageous range of size of particles of additive material prior to the mixing step (a).

4. A method as claimed in claim 1, wherein the additive material is added in the form of a suspension.

5. A method as claimed in claim 1, wherein the additive material includes one or more water soluble substances.

6. A method as claimed in claim 1, wherein the additive material and the carrier particles are mixed for between 0.1 hours and 0.5 hours.

7. A method as claimed in claim 1, wherein the carrier particles are mixed with the additive material using a tumbling blender.

8. A method as claimed in claim 1, wherein the method further includes the step of treating the carrier particles to dislodge small grains from the surfaces of the carrier particles, without substantially changing the size of the carrier particles during the treatment.

9. A method as claimed in claim 8, wherein the mixing step (a) is prior to the treatment step.

10. A method as claimed in claim 8,wherein many of the small grains become reattached to the surfaces of the carrier particles.

11. A method as claimed in claim 8, wherein the treatment is a milling step.

12. A method as claimed in claim 11, wherein the milling step is performed in a ball mill.

13. A method as claimed in claim 12, wherein the carrier particles are milled using plastic balls.

14. A method as claimed in claim 8, wherein the treatment step is carried out in a recirculated low fluid energy mill.

15. A method as claimed in claim 11, wherein the carrier particles are milled for between about 0.25 hours and 6 hours.

16. A method as claimed in claim 1, wherein the powder includes not more than 10% by weight of additive material based on the weight of the powder.

17. A method as claimed in claim 16, wherein the powder includes not more than 5% by weight of additive material based on the weight of the powder.

18. A method as claimed in claim 17, wherein the powder includes not more than 2% by weight of additive material based on the weight of the powder.

19. A method as claimed in claim 1, wherein the particles of additive material have a mass median diameter of not more than 10μm.

20. A method as claimed in claim 1, wherein the particles of additive material have a surface of at least 5 $m^2g^{-1}$.

21. A method as claimed in claim 1, wherein the carrier particles are comprised of one or more crystalline sugars.

22. A method as claimed in claim 21, wherein the carrier particles are particles of lactose.

23. A method as claimed in claim 1, wherein substantially all (by weight) of the carrier particles have a diameter which lies between 20 μm and 1000 μm.

24. A method as claimed in claim 1, wherein the additive material consists of surface active material.

25. A method as claimed in claim 1, wherein the additive material includes one or more compounds selected from amino acids and derivatives thereof, and peptides and polypeptides having a molecular weight from 0.25 to 1000 KDa, and derivatives thereof.

26. A method as claimed in claim 25, wherein the additive material includes an amino acid.

27. A method as claimed in claim 26, wherein the additive material includes or consists of leucine.

28. A method as claimed in claim 1, wherein the additive material includes one or more water soluble materials.

29. A method as claimed in claim 1, wherein the additive material comprises a phospholipid or a derivative thereof.

30. A method as claimed in claim 29, wherein the additive material comprises lecithin.

31. A method as claimed in claim 30, wherein the additive material comprises soya lecithin.

32. A method as claimed in claim 1, wherein the additive material comprises palmitic acid, stearic acid, erucic acid, behenic acid, magnesium stearate, sodium stearyl fumarate, sodium stearyl lactylate, a phosphatidylcholine, a phosphatidylglycerol, a liposomal formulation, lauric acid or a lauric acid salt, or a triglyceride.

33. A method as claimed in claim 1, wherein the additive material comprises magnesium stearate in an amount that forms less than 1.5% by weight of the powder.

34. A method as claimed in claim 1, wherein the additive material includes a plurality of surface active materials.

35. A method as claimed in claim 1, wherein the additive material is an anti-adherent material.

36. A method as claimed in claim 1, wherein the additive material is an anti-friction agent.

37. A method as claimed in claim 1, wherein the additive material includes dipolar ions.

38. A method as claimed in claim 37, wherein the additive material consists of zwitterions.

39. A method as claimed in claim 1, wherein the powder consists of not less than 0.1% by weight of additive particles based on the weight of the carrier particles.

40. A method as claimed in claim 1, wherein the particles of additive material form a discontinuous covering on the surfaces of the carrier particles.

41. A method as claimed in claim 40, wherein the particles of additive material, whilst forming a discontinuous covering on the surfaces of the carrier particles, saturate the surfaces of the carrier particles.

42. A method as claimed in claim 1, wherein the mass median diameter of the active particles is not more than 10μm.

43. A method as claimed in claim 1, wherein the active particles include a $\beta_2$-agonist.

44. A method as claimed in claim 43, wherein the active particles include salbutamol, a salt of salbutamol, salmeterol and/or a salt of salmeterol.

45. A method as claimed in claim 1, wherein the active particles include beclomethasone dipropionate.

* * * * *